(12) United States Patent
Jamison et al.

(10) Patent No.: US 10,989,048 B1
(45) Date of Patent: Apr. 27, 2021

(54) SYSTEMS AND METHODS TO DETECT AND QUANTIFY CONTAMINANTS AND COMPONENTS OF A WELLBORE SERVICING FLUID

(71) Applicant: Halliburton Energy Services, Inc., Houston, TX (US)

(72) Inventors: Dale E. Jamison, Houston, TX (US); William Walter Shumway, Spring, TX (US); Preston Andrew May, Porter, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 16/879,571

(22) Filed: May 20, 2020

(51) Int. Cl.
    *E21B 49/08* (2006.01)
    *G01N 33/28* (2006.01)
(52) U.S. Cl.
    CPC ......... *E21B 49/0875* (2020.05); *G01N 33/28* (2013.01)
(58) Field of Classification Search
    CPC .......................... E21B 49/0875; G01N 33/28
    USPC .............. 73/152.18, 152.01, 152.23, 152.26; 166/250.01
    See application file for complete search history.

(56) References Cited

U.S. PATENT DOCUMENTS

| | | | |
|---|---|---|---|
| 6,276,190 B1 * | 8/2001 | Zamfes ................. | E21B 49/005 73/152.04 |
| 6,386,026 B1 | 5/2002 | Zamfes | |
| 7,100,689 B2 * | 9/2006 | Williams ............... | H04B 1/406 166/264 |
| 7,128,144 B2 * | 10/2006 | Fox ......................... | E21B 49/10 166/100 |
| 7,159,445 B2 | 1/2007 | Böhm et al. | |
| 7,516,654 B2 * | 4/2009 | DiFoggio .............. | E21B 49/081 73/152.23 |
| 7,697,141 B2 | 4/2010 | Jones et al. | |
| 8,186,211 B2 * | 5/2012 | Boult ...................... | E21B 49/08 73/152.27 |
| 8,763,696 B2 | 7/2014 | Bedouet et al. | |
| 9,435,192 B2 * | 9/2016 | Lawrence ............... | E21B 49/08 |
| 9,506,337 B2 * | 11/2016 | Smith ..................... | E21B 47/01 |

(Continued)

FOREIGN PATENT DOCUMENTS

EP           0370548           9/1994

OTHER PUBLICATIONS

Lin, H., Jang, M., & Suslick, K. S. (2011). Preoxidation for Colorimetric Sensor Array Detection of VOCs. Journal of the American Chemical Society, 133(42), 16786-16789.

(Continued)

*Primary Examiner* — Nimeshkumar D Patel
*Assistant Examiner* — Jean F Morello
(74) *Attorney, Agent, or Firm* — Tenley Krueger; C. Tumey Law Group PLLC

(57) ABSTRACT

Systems and methods of the present disclosure generally relate to a detection of interface mixing between downhole materials within a wellbore. A system comprises a sensor configured to detect volatile organic compounds (VOCs). The sensor is in fluid communication with a downhole material recovered from a wellbore, wherein the sensor is fluidly coupled to a circulatory system for the wellbore. The system also includes a system controller in communication with the sensor. The system controller is configured to indicate concentrations of the VOCs.

20 Claims, 14 Drawing Sheets

(56) References Cited

U.S. PATENT DOCUMENTS

| | | |
|---|---|---|
| 10,018,613 B2 | 7/2018 | Potyrailo et al. |
| 10,025,000 B2 | 7/2018 | Monteiro et al. |
| 10,083,258 B2 | 9/2018 | Kauerauf et al. |
| 2012/0178653 A1 | 7/2012 | McClung, III |
| 2013/0175036 A1 | 7/2013 | Hausot |
| 2013/0303929 A1 | 11/2013 | Martino et al. |
| 2016/0238547 A1 | 8/2016 | Park et al. |
| 2018/0045044 A1 | 2/2018 | Ye et al. |
| 2019/0064039 A1* | 2/2019 | Ammar .................... G01N 1/34 |

OTHER PUBLICATIONS

Formation Evaluation, Reservoir Engineering, ICE Core Fluid Analysis Service, Halliburton, H010946, Oct. 2017.
International Search Report and Written Opinion for Application No. PCT/US2020/035110, dated Feb. 16, 2021.

* cited by examiner

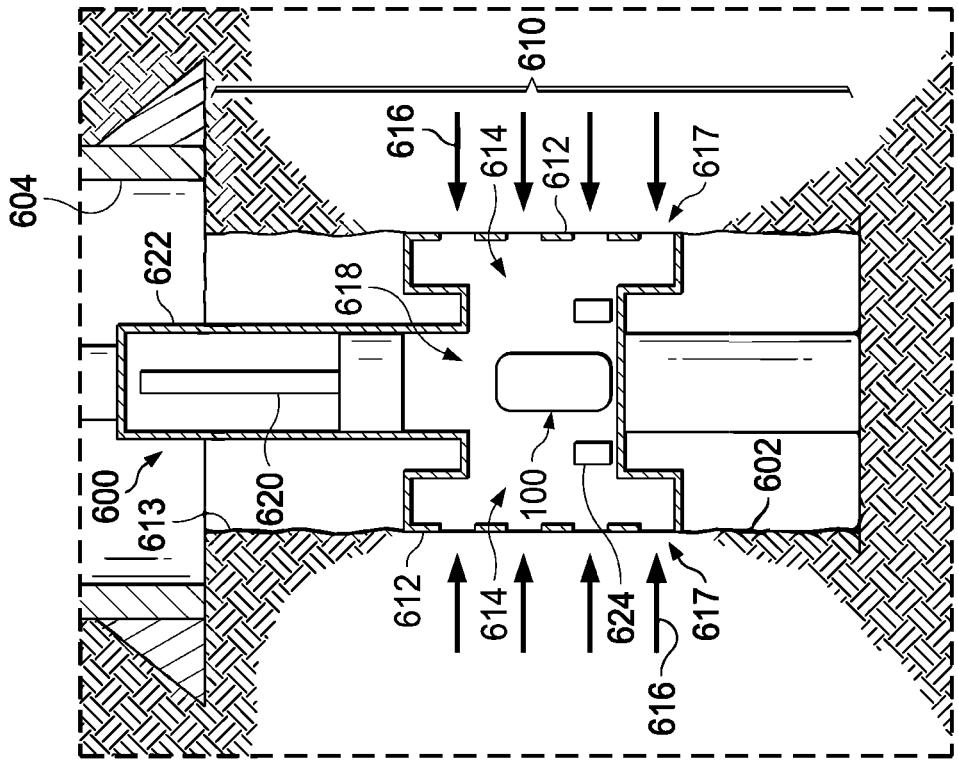
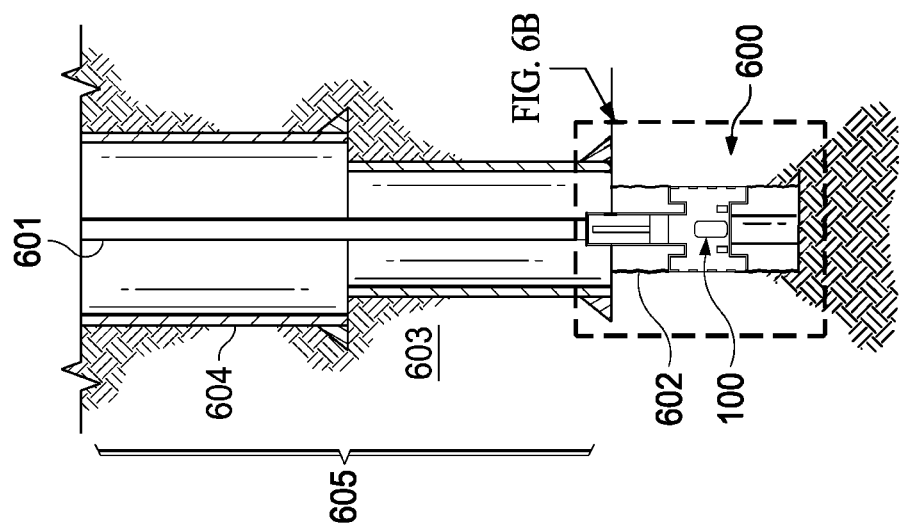
FIG. 6B
FIG. 6A

SYSTEMS AND METHODS TO DETECT AND QUANTIFY CONTAMINANTS AND COMPONENTS OF A WELLBORE SERVICING FLUID

BACKGROUND

During a wellbore cleanup operation, a fluid such as a spacer fluid, may be circulated from the surface, into the wellbore, and back up to the surface to clear the wellbore of fluid and debris that may interfere with downhole operations such as cementing or drilling, for example. Determining content of the fluid and debris recovered from the wellbore, may be useful for managing an effective wellbore cleanup operation.

BRIEF DESCRIPTION OF THE DRAWINGS

These drawings illustrate certain aspects of some examples of the present invention and should not be used to limit or define the invention.

FIG. 6A illustrates a downhole tool that includes the sensor, in accordance with particular examples of the present disclosure;

FIG. 6B illustrates a close-up view of the downhole tool, in accordance with examples of the present disclosure:

DETAILED DESCRIPTION

Figure 1:
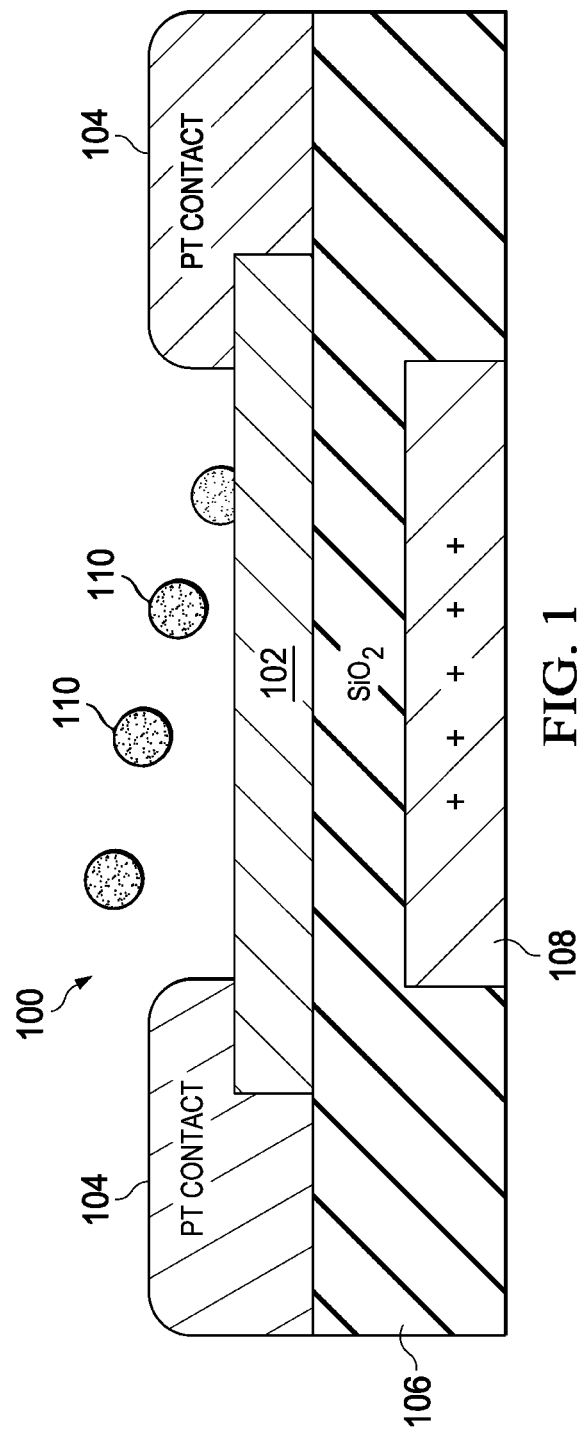
FIG. 1 illustrates a chemical sensor, in accordance with particular examples of the present disclosure.

Systems and methods of the present disclosure generally relate to a real time analysis of subterranean materials with a chemical sensor. Systems and methods of the present disclosure may identify and quantify vapors of a subterranean or downhole material. The vapors may provide indications of the presence of specific compounds or components contained in a composition, as well as a quantity of these materials. This data can provide a basis for adjusting a dosage of various products or components that may be disposed downhole during a subterranean operation such as drilling for example. Wellbore servicing fluid properties may be maintained, managed, and controlled. Non-limiting examples of managed properties include: rheology (e.g., derived from concentration of components), emulsifier content, lubricant content, corrosion inhibitors content, filtrate control components content, thinner content, shale inhibitor content and toxicity to marine life, disposability of a fluid, oil content in drill cuttings, and/or a presence or absence of contaminants such as $CO_2$, $H_2S$, and/or crude oil.

In certain examples, systems and methods of the present disclosure relate to a real time analysis of a condition of a wellbore spacer fluid utilized in a wellbore cleanup operation. Specifically, the systems and methods of the present disclosure may utilize an electronic chemical sensor to determine contamination of the spacer fluid that occurs as the spacer fluid moves through the wellbore during the wellbore cleanup operation. For example, the electronic chemical sensor may detect contamination of a spacer fluid due to interface mixing between spacer fluids, and/or interface mixing between a spacer fluid and a drilling fluid.

In certain examples, the electronic chemical sensor may detect specific volatile components of the spacer fluid. For example, the electronic chemical sensor may detect a presence of certain molecules as well as their quantity within vapors of the spacer fluid. The vapors may provide indications of a presence of specific compounds or components, as well as a quantity of contaminants in the spacer fluid. The electronic chemical sensor does not rely on spectroscopy or another co-detection technique to elucidate specific molecules.

Utilization of the electronic chemical sensor allows for a real time modification of the wellbore cleanup operation. For example, real time adjustments to a spacer fluid volume, spacer fluid viscosity, spacer fluid chemical additions, pipe rotation, contact times and/or pump rates, may be based on a real time condition of the spacer fluid in the wellbore. For example, spacer fluid volumes may be increased due to an undesirable level of contaminants detected in the spacer fluid. Determining spacer fluid contamination in real time may assist in ensuring that the wellbore cleanup operation is effective.

Additionally, recycling or recovery of fluids may be a viable application of systems and methods of the present disclosure. For example, for the reclamation of brines from drill-in fluids, signals from organic additives may be monitored during reclamation processes. A decrease in a quantity or intensity of the signals may be used to determine when the fluid had been processed sufficiently to recover only the brine phase, while stripping out unwanted organic components, thereby saving processing time, as well as preventing an overtreatment of breakers and chemicals, to avoid excessive treatment times.

In some examples, the chemical sensor may analyze organic materials associated with drill cuttings. The chemical sensor may identify a species of organic molecules in the drill cuttings as well as provide a measure of the quantity of each species, in real time. This data may be used to manage a trajectory of the wellbore and the ultimate wellbore production. In some examples, knowledge gained from analyzing the drill cuttings may be used to assist in decisions impacting directional drilling and measured depth. Drilling software may determine a source location of the drill cuttings via drill cuttings transport models.

In other examples, the chemical sensor may be disposed within a downhole tool such as measurement while drilling tool. The downhole tool may sample formation fluid, drilling fluid, and/or drill cuttings. The downhole tool may pull a vacuum or otherwise volatilize or vaporize the sample for analysis by the chemical sensor to determine a presence and concentration of specific volatile components. The chemical sensors along with models and artificial intelligence (AI), may provide details of chemical compositions of subterranean formations. In some examples, results of sampling the subterranean material, in real time, may change a planned trajectory of a well. Additionally, results of sampling the subterranean material may change basin modeling and pore pressure predictions downhole, as well as change drilling conditions such as flow rate and/or rate of penetration (ROP), for example.

FIG. 1 illustrates an electronic chemical sensor 100 ("sensor 100") in accordance with particular examples of the present disclosure. In certain examples, the sensor 100 may include a nanotube 102 disposed between and in contact with platinum contacts 104. A layer 106 comprising silicon dioxide may be disposed adjacent to and in contact with the platinum contacts 104 and the nanotube 102. A polysilicon gate 108 may be disposed adjacent to the layer 106. The layer 106 may separate the polysilicon gate 108 from the platinum contacts 104 and the nanotube 102. The sensor 100 is sensitive to volatile organic compounds ("VOC"). The VOCs may be added to treatment components in known quantities as chemical tags, so that the treatment components' presence and concentration may be quickly determined. For example, wellbore cleanup fluids, such as a spacer fluid, for example, may have unique VOC signatures or chemical tags that can be analyzed to determine the spacer fluid's contamination and condition after a wellbore cleanup operation. Non-limiting examples of VOCs may include base oils, crude oils, emulsifiers, glycols, resins, methane, carbon dioxide, hydrogen sulfide, or combinations thereof. In some cases, the chemical tags may include environmentally safe materials, such as fragrances, for example.

Vapor molecules 110 of a wellbore fluid such as a spacer fluid, for example, may contact the nanotube 102, thereby allowing the sensor 100 to detect, identify, and quantify specific volatile components, such as the VOCs, contained in the wellbore fluid. The sensor 100 is a non-limiting example, and other suitable sensors may be utilized, as should be understood by one having skill in the art, with the benefit of this disclosure.

Figure 2C:
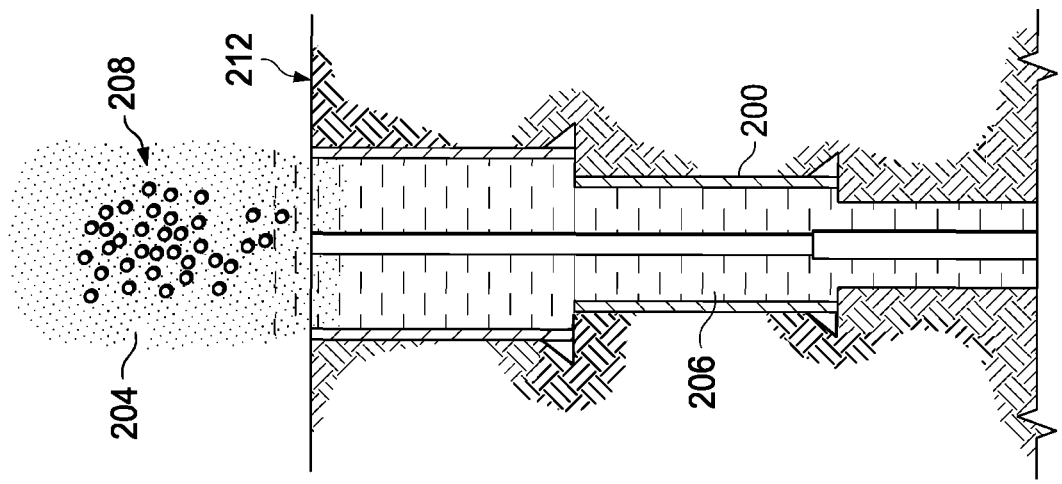
FIGS. 2A-2C illustrate a sequence of interface mixing between downhole materials, in accordance with particular examples of the present disclosure.
Figure 2B:
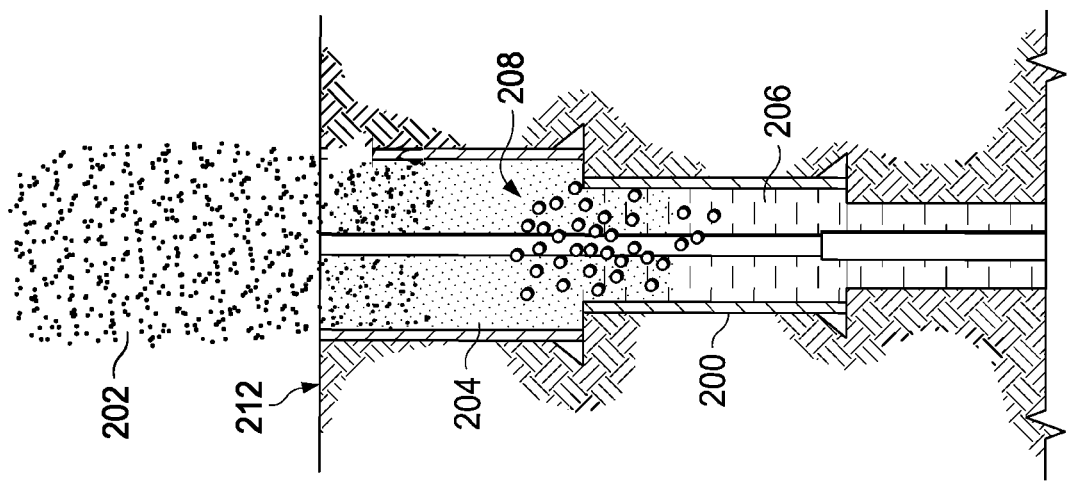
Figure 2A:
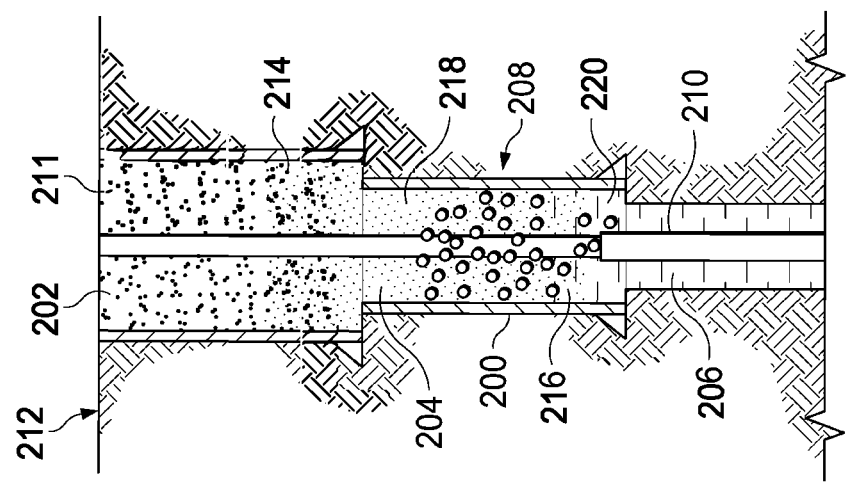

FIGS. 2A-2C illustrate a sequence of interface mixing between various materials in a wellbore 200 during a wellbore cleanup operation, in accordance with particular examples of the present disclosure. FIG. 2A illustrates the wellbore 200 containing a first spacer fluid 202, a second spacer fluid 204, and a third spacer fluid 206, and formation debris 208 such as drill cuttings, for example. The first spacer fluid 202 may be or include a filter cake breaker. The second spacer fluid 204 may be or include a highly viscosified sweep to remove debris. The third spacer fluid 206 may be or include a base oil. A fourth spacer fluid (not shown) may be or include a wellbore clean up fluid. A fifth spacer fluid (not shown) may be or include a brine. In certain examples, the aforementioned spacer fluids may be repeated or introduced into a downhole environment in different orders.

The first spacer fluid 202 may be pumped into the wellbore 200 via a downhole tubular 210 (e.g., casing or drill pipe) to displace or carry the formation debris 208 to a surface 212 above the wellbore 200 via an annulus 211, for example. After the first spacer fluid 202 is pumped downhole, the second spacer fluid 204 may be pumped into the wellbore 200 via the downhole tubular 210 to displace or carry the formation debris 208 to the surface 212, as well as displace or move the first spacer fluid 202 to the surface 212. After the second spacer fluid 204 is pumped downhole, the third spacer fluid 206 may be pumped into the wellbore 200 via the downhole tubular 210 to displace or carry the formation debris 208 to the surface 212, as well as displace or move the second spacer fluid 204 to the surface 212.

A mixing interface 214 is illustrated between the first spacer fluid 202 and the second spacer fluid 204. A mixing interface 216 is illustrated between the second spacer fluid 204 and the third spacer fluid 206. Additionally, a mixing interface 218 is illustrated between the formation debris 208 and the second spacer fluid 204, and a mixing interface 220 is illustrated between the formation debris 208 and the third spacer fluid 204.

FIG. 2B illustrates a first stage of up-hole movement of the spacer fluids 202, 204, and 206, as well as the formation debris 208, during the wellbore cleanup operation, in accordance with particular examples of the present disclosure. As shown on FIG. 2B, the third spacer fluid 206 and the second spacer fluid 204 have displaced the first spacer fluid 202 to the surface 212 of the wellbore 200. The formation debris 208 has also moved up-hole due to up-hole movement of the second and third spacer fluids 204 and 206.

FIG. 2C illustrates a second stage of up-hole movement of the spacer fluids 204 and 206, as well as the formation debris 208, during the wellbore cleanup operation, in accordance with particular examples of the present disclosure. As shown on FIG. 2C, the first spacer fluid 202 (shown on FIG. 2B) has been displaced from the wellbore 200 and is therefore not illustrated. The third spacer fluid 206 has displaced the second spacer fluid 204 and the formation debris 208 to the surface 212 of the wellbore 200.

As the first spacer fluid 202, the second spacer fluid 204, the third spacer fluid 206, and the formation debris 208 exit the wellbore 200, the sensor 100 (shown on FIG. 1) may detect a presence of each of the first spacer fluid 202, the second spacer fluid 204, the third spacer fluid 206, and the formation debris 208, and quantify their presence. In some examples, a turbidity or density meter (not shown) may be used in conjunction with the sensor 100 to assist in an analysis (e.g., identification) and differentiation of the spacer fluids 202, 204, 206, and/or the formation debris 208.

Figure 3:
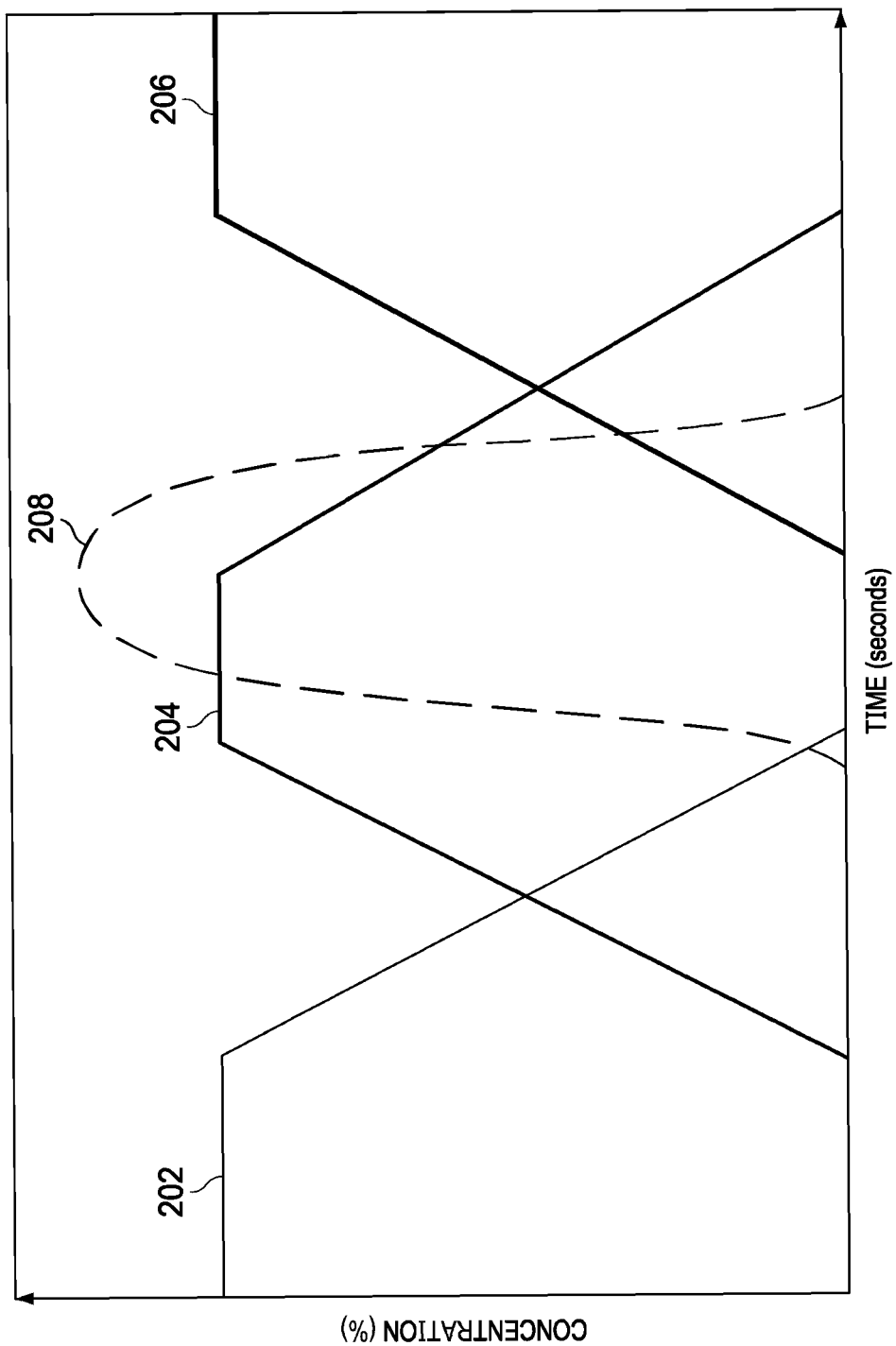
FIG. 3 illustrates a plot of concentrations of the downhole materials against time, in accordance with particular examples of the present disclosure.

FIG. 3 illustrates measured concentration (e.g., a percentage) of the spacer fluids 202, 204, 206 and the formation debris 208 against time (e.g., seconds), during the wellbore cleanup operation, in accordance with particular examples of the present disclosure. As illustrated, a concentration of the first spacer fluid 202 may decrease as a concentration of the second spacer fluid 204 increases. A concentration of the formation debris 208 may increase as the concentration of second spacer fluid 204 increases and the concentration of the first spacer fluid 202 decreases. The concentration of the formation debris 208 may decrease while the concentration of the second spacer fluid 204 decreases and a concentration of the third spacer fluid 206 increases.

Figure 4:
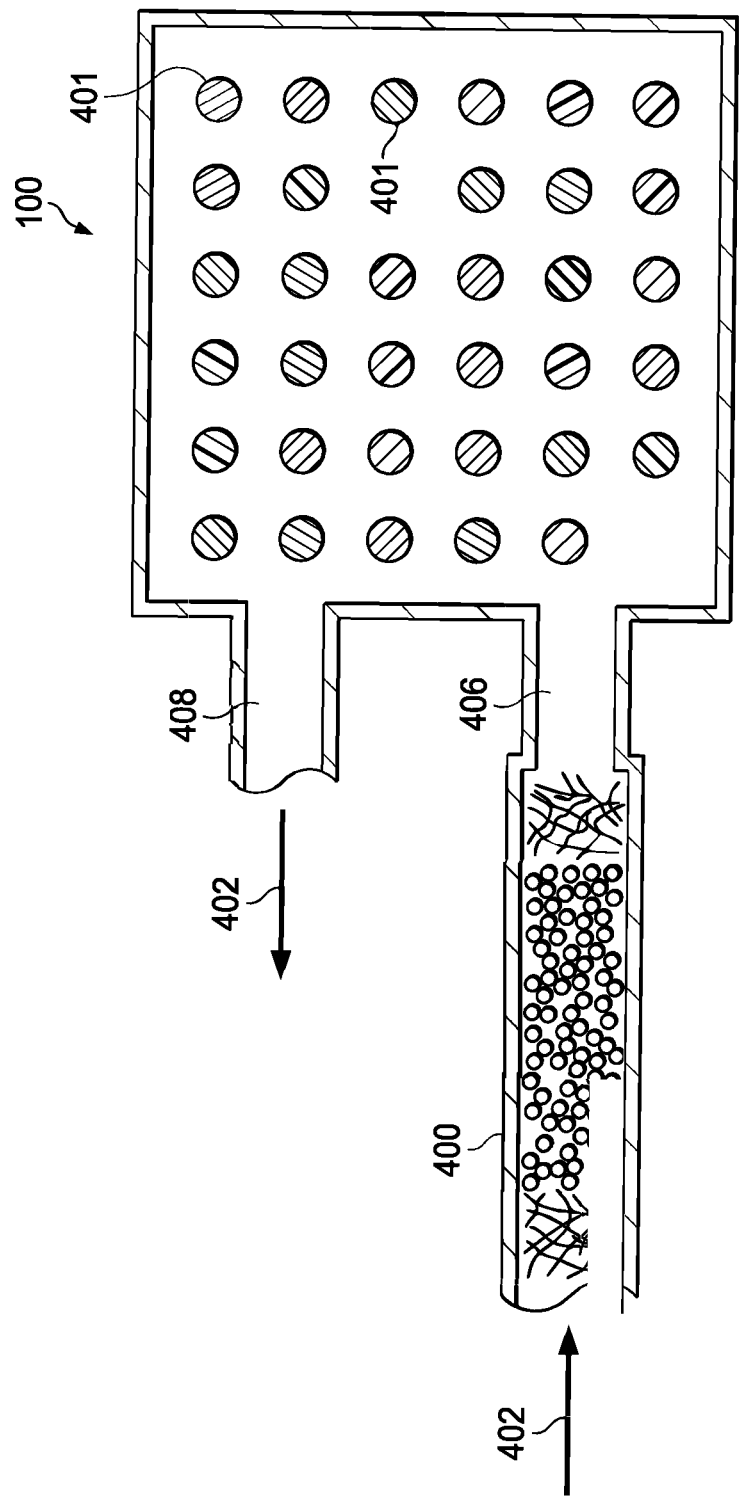
FIG. 4 illustrates a sensor utilized for sensing volatile organic compounds, in accordance with particular examples of the present disclosure.

FIG. 4 illustrates a chemical pretreatment tube 400 that may treat VOCs 402 before their detection by the sensor 100, in accordance with particular examples of the present disclosure. Identification of VOCs or other gaseous analytes may be improved by the chemical pretreatment, either by treating a liquid itself or a gaseous phase. The sensor 100 may include an array of nanocomposites 401 that include carbon nanotubes, conducting polymers, metallic and non-metallic nanoparticles, to detect a wide range of VOCs, in some examples.

The pre-treatment tube 400 may be configured for pre-treatments such as oxidation, reduction, acids, bases, electrochemistry, thermal energy, microwave energy, or ultraviolet irradiation, for example. In certain examples, a gaseous phase containing the VOCs 402 may pass through the pre-treatment tube 400 which may include a polytetrafluoroethylene ("PTFE") tube packed with chromic acid and/or silica. The pre-treatment tube 400 may be in fluid communication with an inlet 406 of the sensor 100. The VOCs 402 may pass into the pre-treatment tube 400 and into the sensor 100 via the inlet 406. The VOCs 402 may then exit the sensor 100 via the outlet 408. In certain examples, a pre-treatment such as a pre-oxidation of the gaseous phase containing the VOCs 402 may improve detection by up to about 300-fold when compared to a colorimetric assay of the gaseous phase containing the VOCs 402.

Figure 5A:
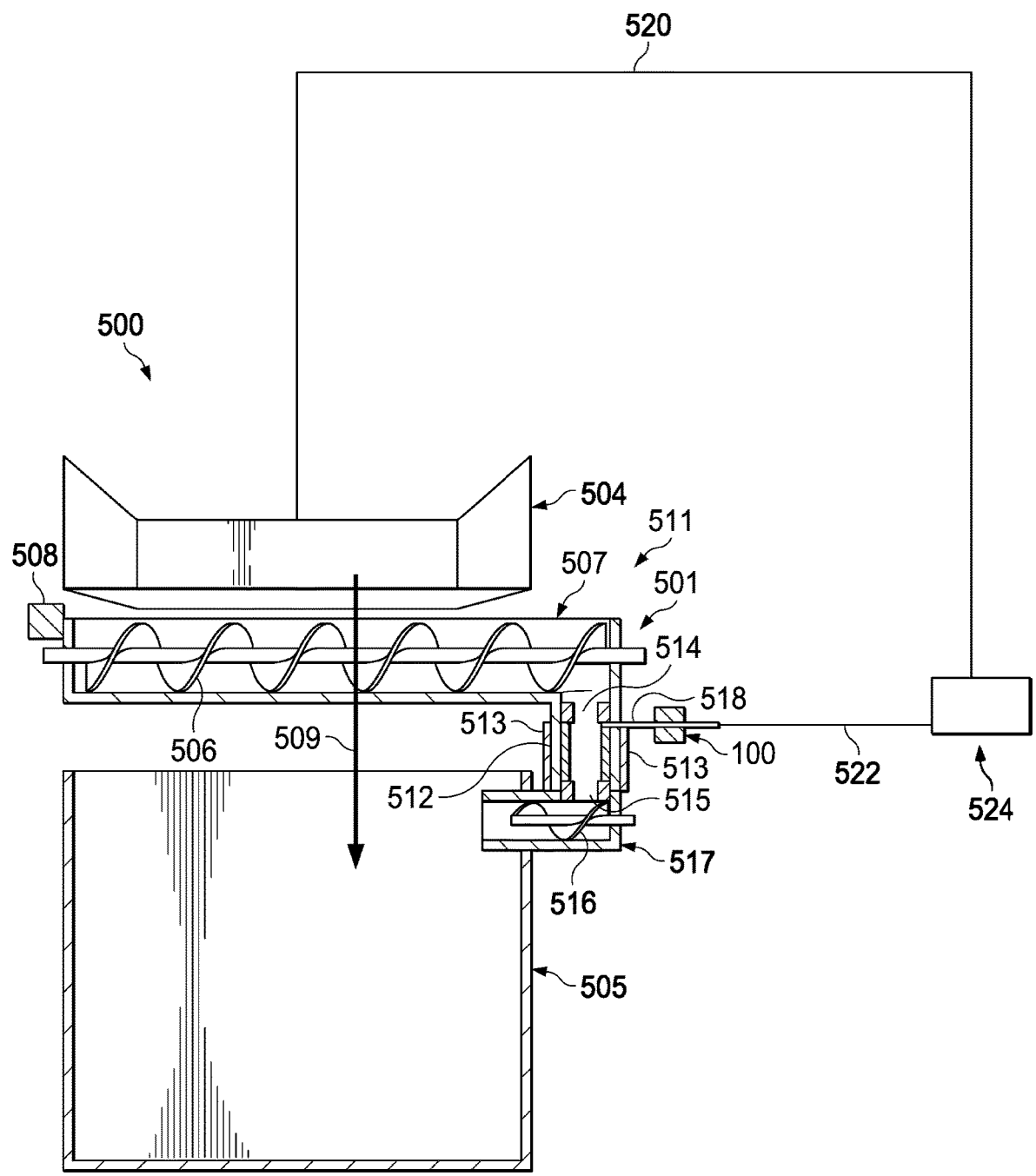
FIGS. 5A-5F illustrate an operative sequence of a solids control device that includes the sensor, in accordance with particular examples of the present disclosure.

FIG. 5A illustrates a front perspective view of a system 500 that includes the sensor 100 to analyze organic materials associated with drill cuttings (not shown), in accordance with particular examples of the present disclosure. The system 500 may include a solids control device 501, such as, for example, a drill cuttings or shale shaker, a centrifuge, a hydro-cyclone, a separator (including magnetic and electrical separators), a de-silter, a de-sander, a separator, a filter (e.g., diatomaceous earth filters), a heat exchanger, or any fluid reclamation equipment. As previously noted, the sensor 100 may analyze organic materials associated with the drill cuttings. The sensor 100 may identify a species of organic molecules in the drill cuttings as well as determine a quantity of each species, in real time.

The solids control device 501 may include a trough 504 such as a vibrating surface or screen, to receive the drill cuttings (not shown) from a flow line (not shown) that is in fluid communication with a wellbore (not shown), for example. A drill cuttings box or receptacle 505 may be disposed below the trough 504 to receive the drill cuttings that fall from the trough 504. The solids control device 501 may also include a first housing 507 including a first auger 506 that is configured to rotate within the first housing 507. The first housing 507 may be positioned between the trough 504 and the receptacle 505. The first housing 507 may be configured to extend from a retracted position to intercept the drill cuttings that fall from the trough 504. During recovery of the drill cuttings with the first housing 507, the drill cuttings do not fall into the receptacle 505.

As shown, the first housing 507 is in a forward or actuated position to receive the drill cuttings from the trough 504. The first housing 507 may also retract underneath the trough 504 after collection of a sample of the drill cuttings is complete, in some examples. For example, the first housing 507 may be coupled to a hydraulically actuated arm 508 for extending and retracting the first housing 507 into and out of a flow path 509 of the drill cuttings from the trough 504 to the receptacle 505.

Additionally, the first housing 507 may be in fluid communication with a testing chamber or cell 512 for analyzing the drill cuttings. In some examples, the cell 512 may be coupled to the first housing 507 to form a testing assembly 511. The first auger 506 may rotate to direct the drill cuttings into the cell 512 for analysis. The cell 512 may include an inlet valve 514 and an outlet valve 515. The cell 512 is a non-limiting example and other suitable testing cells or chambers may be utilized, as should be understood by one having skill in the art, with the benefit of this disclosure.

The inlet valve 514 and the outlet valve 515 may be on opposing ends of the cell 512. Non-limiting examples of the inlet valve 514 and the outlet valve 515 may include pinch valves, solenoid valves, or other types of suitable valves as should be understood by one having skill in the art with the benefit of this disclosure. The inlet valve 514 may be adjacent to the first auger 506 and may open to allow the drill cuttings into the cell 512 while the outlet valve 515 is closed. In some examples, the first housing 507 may extend into the flow path 509 and the first auger 506 may rotate to direct the drill cuttings into the cell 512, upon opening of the inlet valve 514.

The inlet valve 514 may close after a desired or threshold amount of the drill cuttings is received within the cell 512. In some examples, the first auger 506 ceases to rotate and/or the first housing 507 may retract, upon closing of the inlet valve 514. In some examples, after the collection of the sample of the drill cuttings within the cell 512, the testing assembly 511 may retract underneath the trough 504 such as to not interfere with or obstruct the flow path 509, thereby allowing the drill cuttings to fall from the trough 504 into the receptacle 505 while analysis or testing of the drill cutting is performed.

Upon closing of the inlet valve 514, vapor from the drill cuttings passes into the cell 512 for analysis. The vapor may pass into the cell 512 via a conduit 518. The conduit 518 may extend from the cell 512 to the sensor 100. In certain examples, the conduit 518 may be or include the pretreatment tube 400 (e.g., shown on FIG. 4). In certain examples, the cell 512 may include heaters 513 (e.g., electrical heaters) to vaporize the drill cuttings contained within the cell 512. The heaters 513 may be integrated into portions or walls of the cell 512, for example. The heaters 513 may be utilized to vaporize less volatile organics such as resins, tars and/or asphaltene materials, for example. In some examples, the drill cuttings may not be heated with the heaters 513 because the drill cuttings may be emitting vapors as they flow from a subterranean formation. Upon completion of the vapor analysis, the outlet valve 515 opens to release the drill cuttings from the cell 512.

In some examples, the cell 512 may be disposed between the first housing 507 and a second housing 517. A second auger 516 may be disposed within the second housing 517. The second auger 516 may be in fluid communication with the cell 512. The second auger 516 may be adjacent to the outlet valve 515. The second auger 516 may extend from the cell 512 to the receptacle 505. The second housing 517 may receive expelled drill cuttings and the second auger 516 may rotate to direct the drill cuttings into the receptacle 505. In some examples, the second auger 516 ceases to rotate upon closing of the outlet valve 515 and may begin rotation upon opening of the outlet valve 515.

The system 500 may further include a system controller 524 (e.g., a programmable logic controller) that is in communication (e.g., wires 520 and 522 or wireless) with the various components of the system 500. The system controller 524 may control and operate the system 500. The system controller 524 may include any instrumentality or aggregate of instrumentalities operable to compute, estimate, classify, process, transmit, receive, retrieve, originate, switch, store, display, manifest, detect, record, reproduce, handle, or utilize any form of information, intelligence, or data for business, scientific, control, or other purposes. The system controller 524 may be any processor-driven device, such as, but not limited to, a personal computer, laptop computer, smartphone, tablet, handheld computer, dedicated processing device, and/or an array of computing devices. In addition to having a processor, the system controller 524 may include a server, a memory, input/output ("I/O") interface(s), and a network interface. The memory may be any computer-readable medium, coupled to the processor, such as RAM, ROM, and/or a removable storage device for storing data and a database management system ("DBMS") to facilitate management of data stored in memory and/or stored in separate databases. The system controller 524 may also include display devices such as a monitor featuring an operating system, media browser, and the ability to run one or more software applications. Additionally, the system controller 524 may include non-transitory computer-readable media. Non-transitory computer-readable media may include any instrumentality or aggregation of instrumentalities that may retain data and/or instructions for a period of time.

Figure 5B:
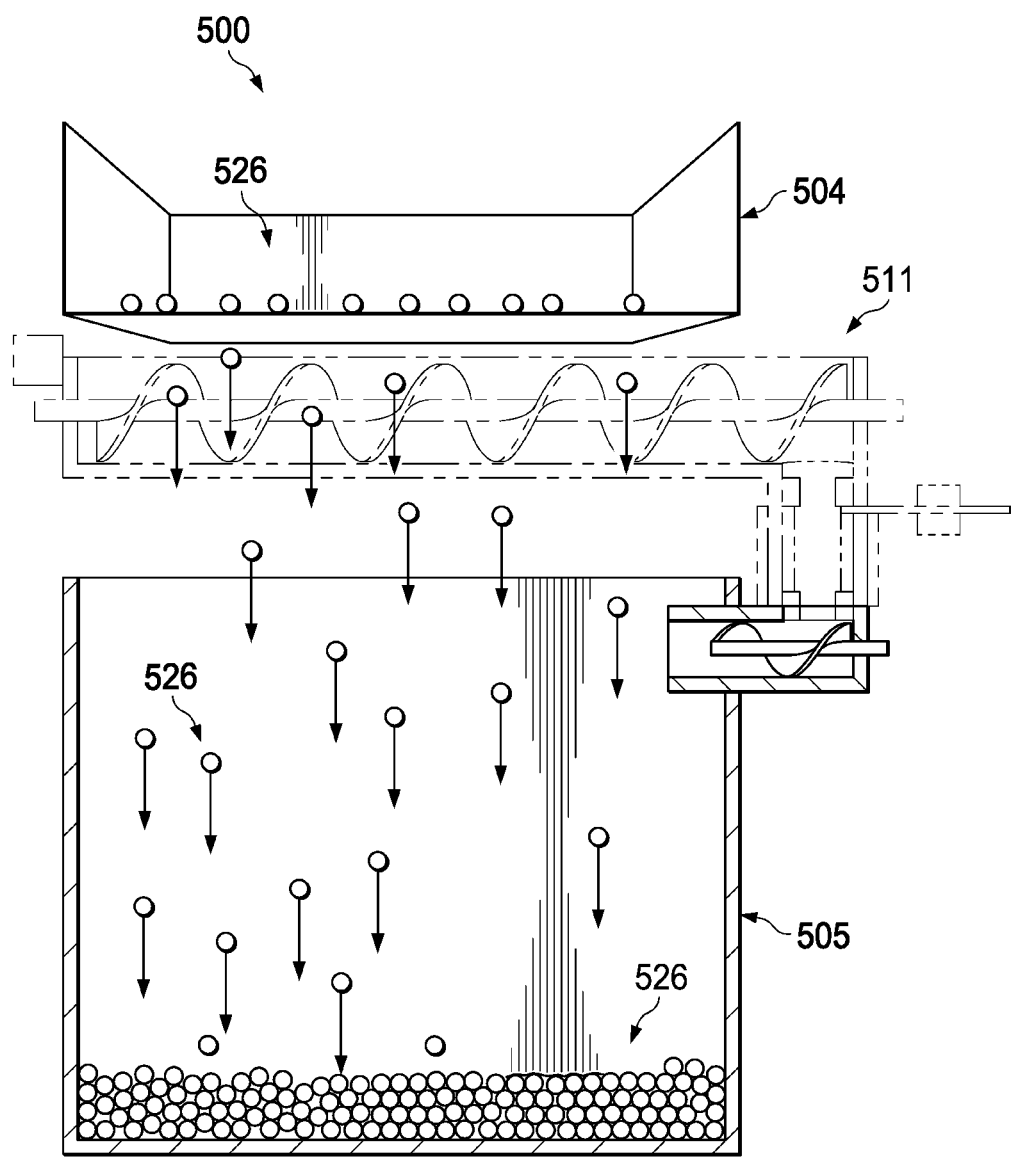

FIG. 5B illustrates the system 500 during a non-testing stage, in accordance with particular examples of the present disclosure. As illustrated, the testing assembly 511 has been retracted underneath the trough 504 to allow the trough 504 to pass the drill cuttings 526 into the receptacle 505. The drill cuttings 526 are not being directed to the cell 512 (e.g., shown on FIG. 5A) for testing during this stage of operation. Rather, the drill cuttings 526 move or fall into the receptacle 505 for disposal, for example.

Figure 5C:
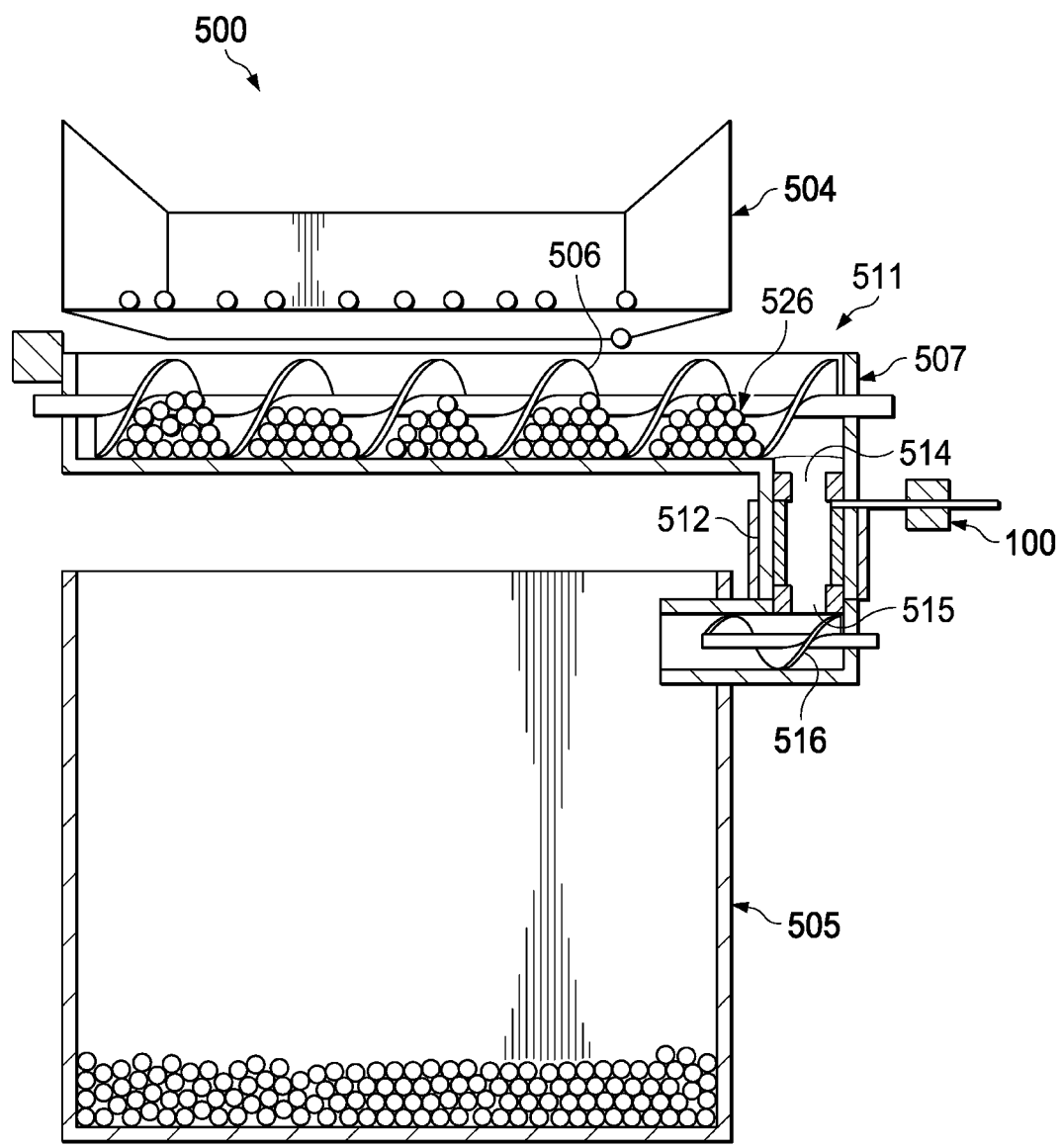

FIG. 5C illustrates the system 500 during a first phase of a drill cuttings testing sequence, in accordance with particular examples of the present disclosure. As illustrated, the testing assembly 511 has been actuated such that the first housing 507 and the cell 512 are in a forward position to recover samples of the drill cuttings 526 falling from the trough 504. The drill cuttings 526 may move into the first housing 507 instead of moving or falling into the receptacle 505. The first auger 506 rotates to direct the drill cuttings 526 into the cell 512. The inlet valve 514 and the outlet valve 515 may be open during this first phase of the testing sequence. In some examples, the second auger 516 does not rotate during this phase.

Figure 5D:
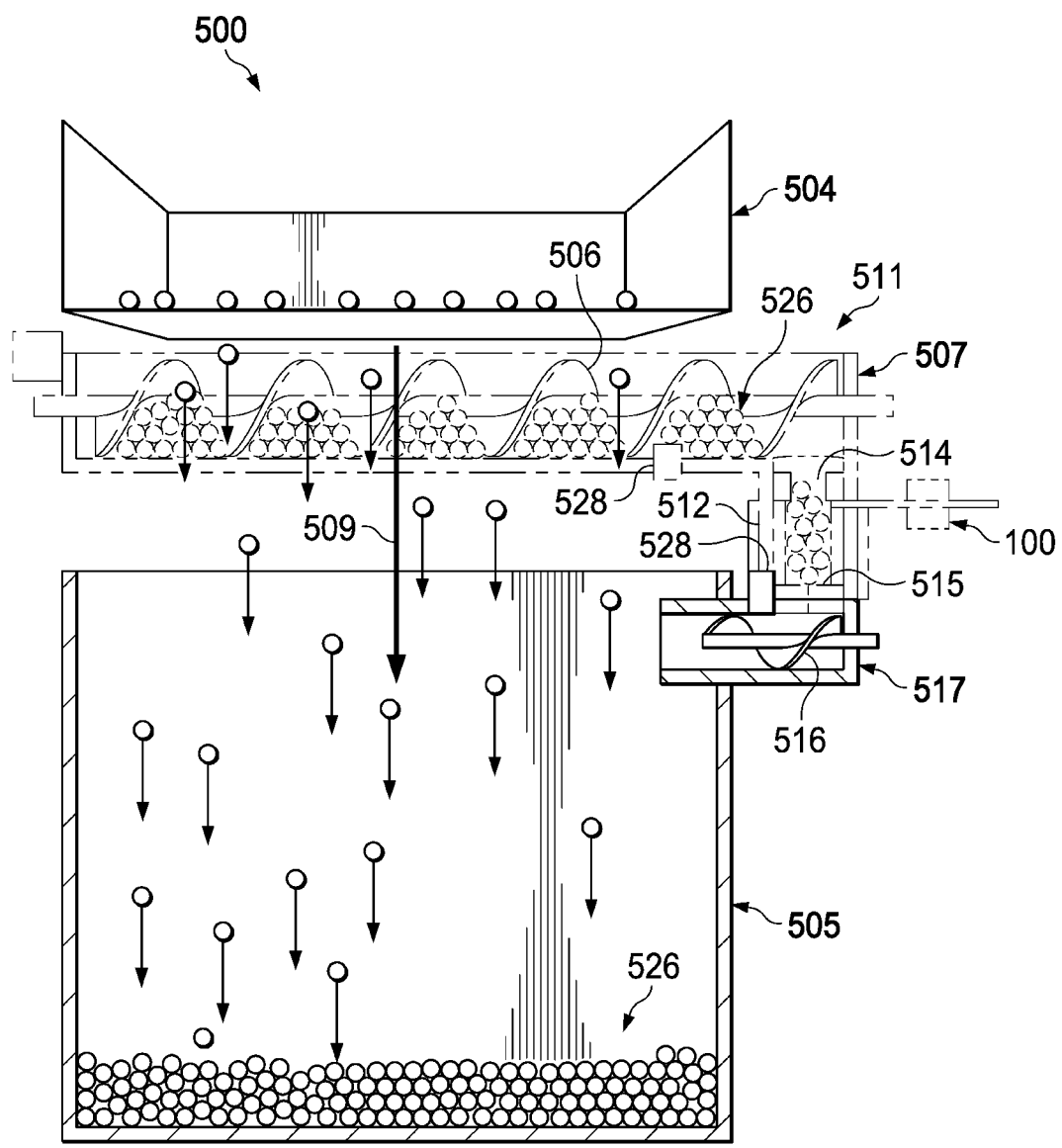

FIG. 5D illustrates the system 500 during a second phase of the drill cuttings testing sequence, in accordance with particular examples of the present disclosure. The inlet valve 514 may open, and the outlet valve 515 may close to allow a sample or a sufficient amount of the drill cuttings 526 to fill the cell 512. In certain examples, the first housing 507 and the cell 512 may include sensors 528 such as a scale and/or pressure sensor to detect a sufficient amount of the drill cuttings 526. After collecting the sample of the drill cuttings 526 within the cell 512, the testing assembly 511 may retract underneath or away from the trough 504 such as to not interfere with or obstruct the flow path 509, thereby allowing the drill cuttings 526 to move from the trough 504 into the receptacle 505 while analysis or testing of the drill cuttings 526 is performed. In the retracted position, as illustrated, the first auger 506 may continue to rotate to direct the drill cuttings 526 into the cell 512, as necessary, to fill the cell 512 with the drill cuttings 526 for analysis, in some examples.

Figure 5E:
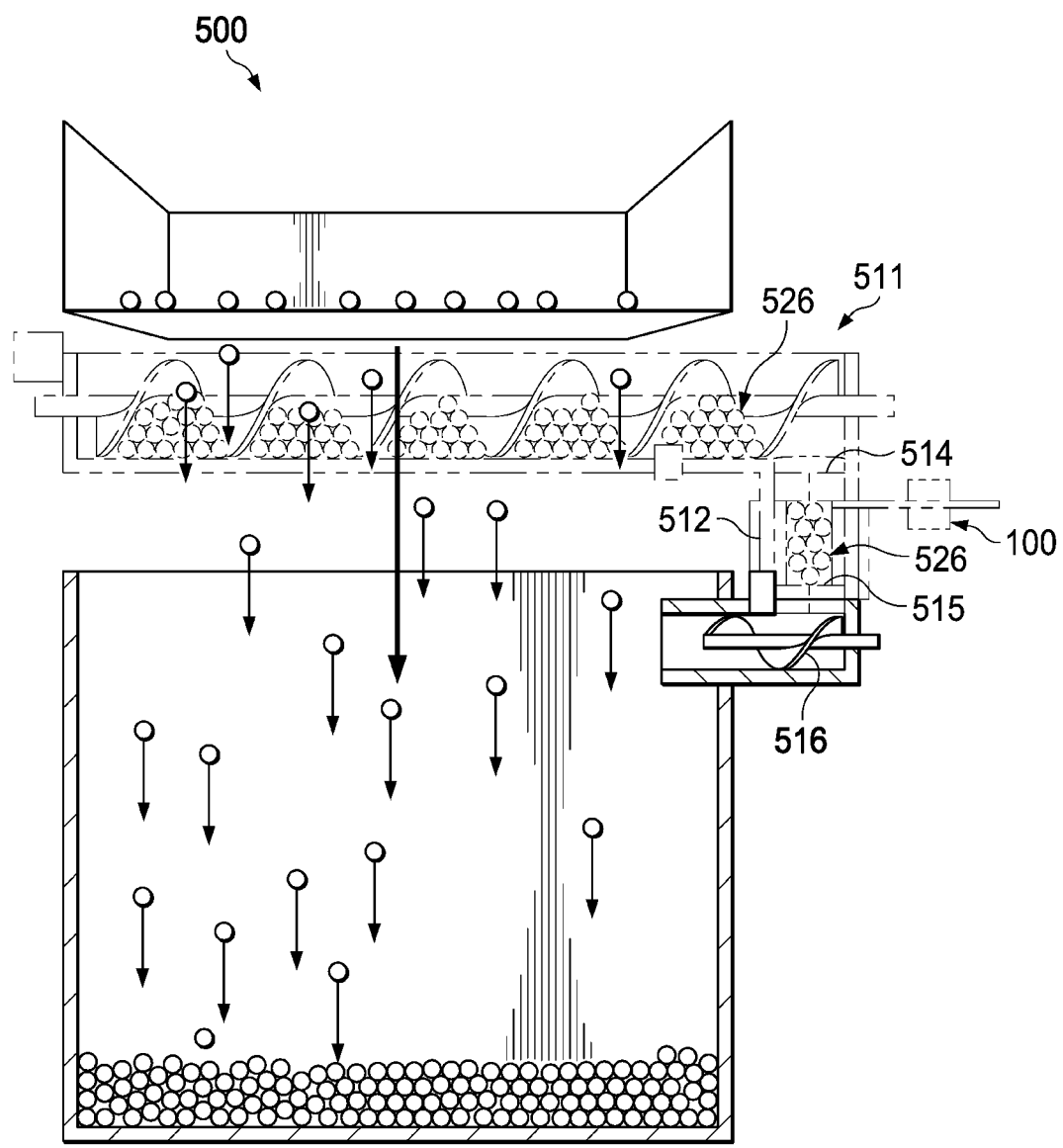

FIG. 5E illustrates the system 500 during a third phase of the drill cuttings testing sequence, in accordance with particular examples of the present disclosure. While the testing assembly 511 is in the retracted position and after collecting the sample of the drill cuttings 526 within the cell 512, the inlet valve 514 may close. The outlet valve 515 may remain closed. After closure of the inlet valve 514, vapors from the drill cuttings 526 may pass from the cell 512 to the sensor 100 for analysis. The second auger 516 may or may not rotate.

Figure 5F:
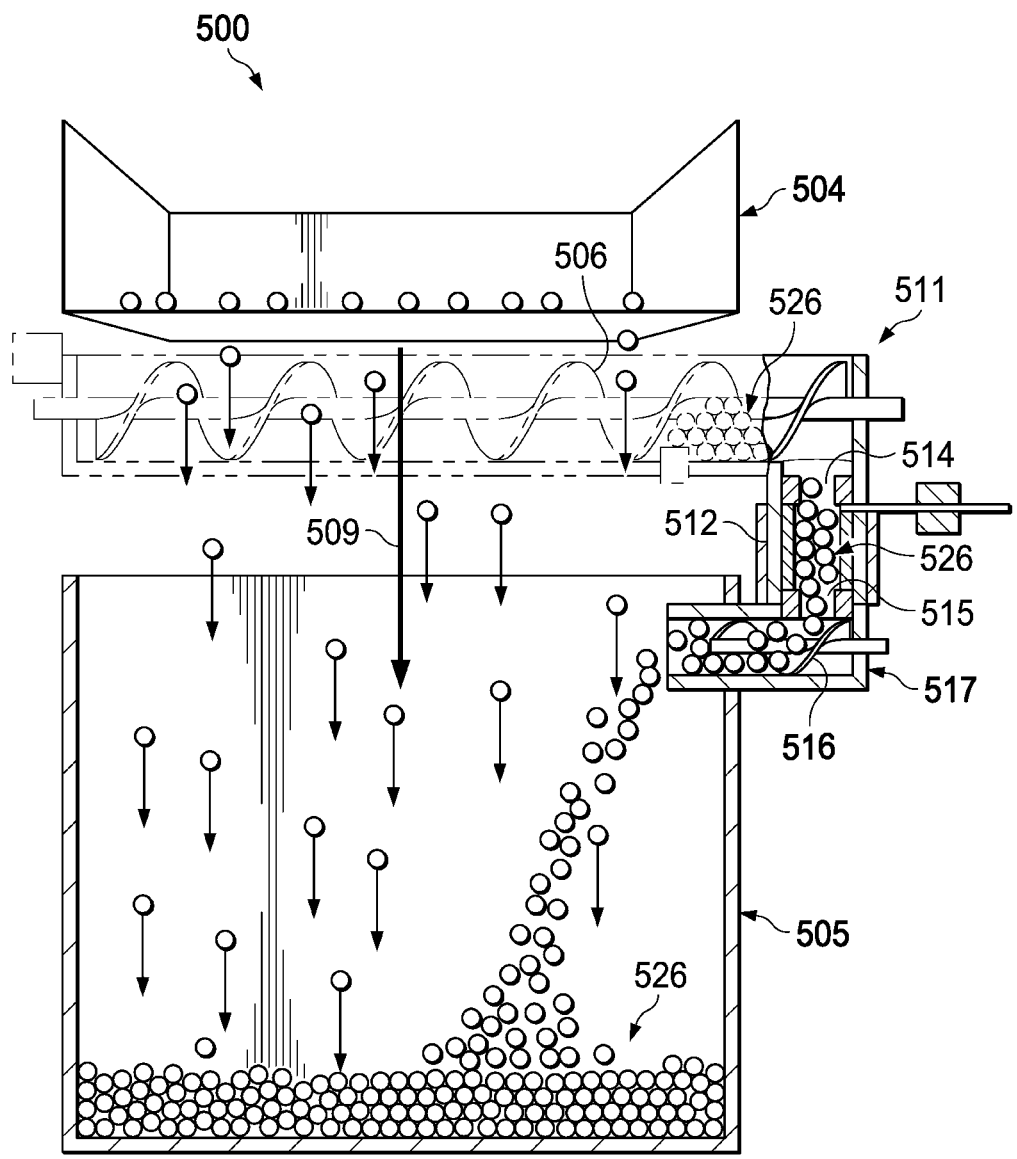

FIG. 5F illustrates the system 500 during a fourth phase of the drill cuttings testing sequence, in accordance with particular examples of the present disclosure. After analyzing the vapors, the testing assembly 511 may move forward (e.g., partial extension) such that the outlet valve 515 of the cell 512 is positioned over a portion of the second auger 516, and the testing assembly 511 does not obstruct the flow path 509 for the drill cutting 526 that are in the trough 504. After alignment between the outlet valve 515 of the cell 512 and the second housing 517, the inlet valve 514 and the outlet valve 515 may open. The drill cuttings 526 may be released into the second housing 517 as the second auger 516 rotates, thereby directing the drill cuttings 526 into the receptacle 505. Additionally, the first auger 506 may rotate to direct any remaining drill cuttings 526 from the first housing 507 through the cell 512 and into the second housing 517 for disposal into the receptacle 505.

FIG. 6A illustrates a downhole tool 600 including the sensor 100, in accordance with particular examples of the present disclosure. The tool 600 may be attached to a drill string 601, for example. In certain examples, the tool 600 may be a reservoir description tool (RDT). The tool 600 may be disposed in a wellbore 602 that extends into a subterranean formation 603. Casing 604 may be disposed in a portion 605 of the wellbore 602.

FIG. 6B illustrates a close-up view of the downhole tool 600, in accordance with examples of the present disclosure. As shown, the casing 604 may be disposed up-hole to an uncased or open hole section 610 of the wellbore 602. A portion of the tool 600 may be disposed in the open hole section 610.

The tool 600 may include sealing pads 612 to seal against a wall 613 of the wellbore 602. The sealing pads 612 may be hydraulically actuated to press against the wall 613 of the wellbore 602. The sealing pads 612 may include internal passages 614 to receive formation fluid 616 via ports 617 of the sealing pads 612. The internal passages 614 fluidly couple the ports 617 to an internal chamber 618 that includes the sensor 100. The internal pressure of the internal chamber 618 may be lowered with a pump that may include a piston 620. The piston 620 may be movably disposed within a cylinder 622 that extends longitudinally within the tool 600. A portion of the piston 620 may be exposed to the fluid 616 that enters the internal chamber 618. As the piston 620 moves away from the internal chamber 618, the piston 620 draws a portion of the fluid 616 into the cylinder 622, thereby creating a vacuum to reduce the internal pressure within the internal chamber 618. This reduction in the internal pressure may cause vaporization of VOCs. The presence and quantity of the VOCs may be detected with the sensor 100. In some examples, the formation fluid 616 that enters the tool 600 may be heated with electrical heaters 624 that may be disposed within the internal chamber 618. The heaters 624 may be utilized to vaporize less volatile organics such as resins, tars and/or asphaltene materials, for example. Although not illustrated, the tool 600 may be in communication with the system controller 524 (e.g., shown on FIG. 5A) to operate the tool 600 via mud pulse telemetry, for example.

Figure 7A:
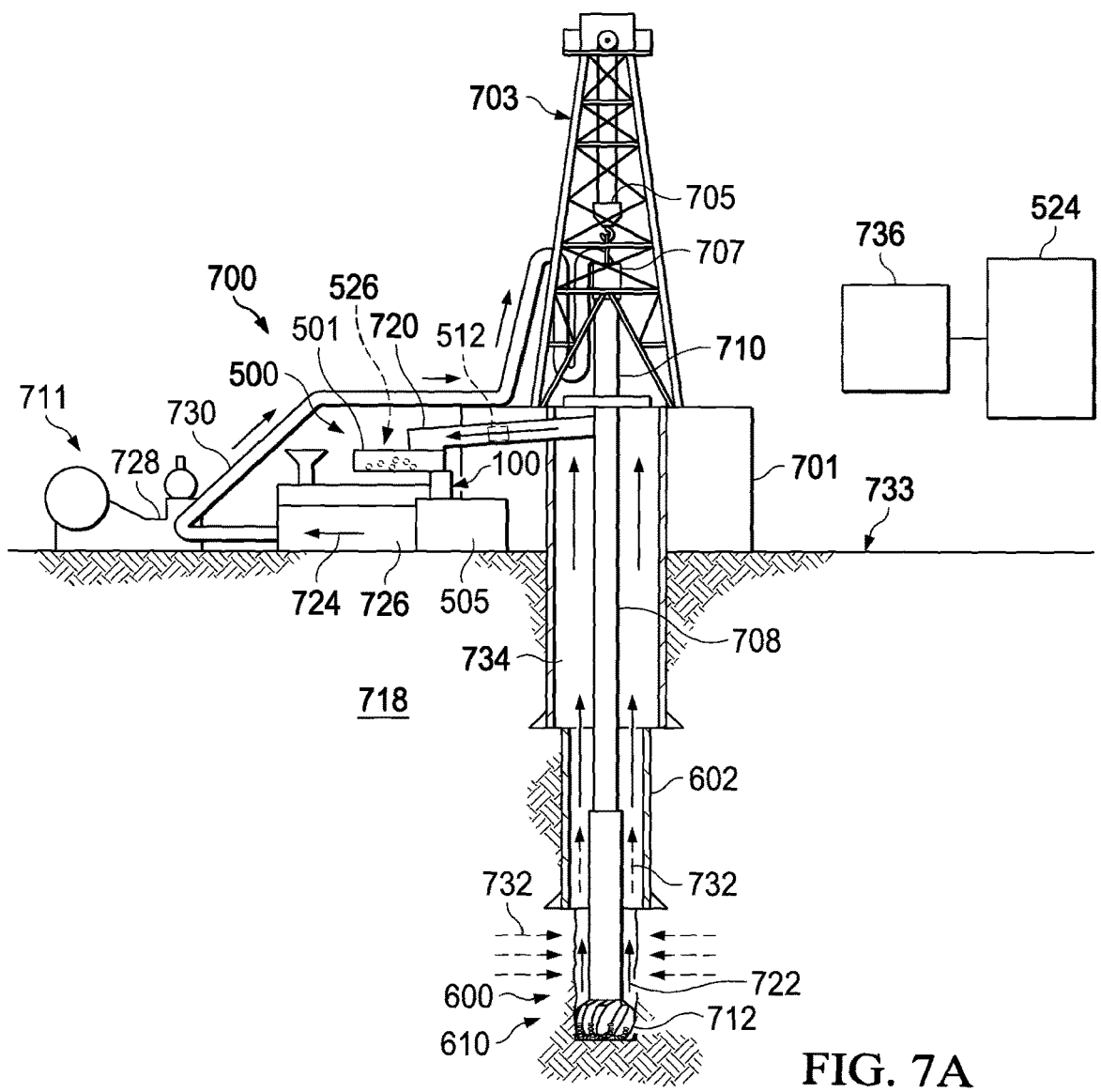
FIG. 7A illustrate an early warning detection system including the sensor.

FIG. 7A illustrates an early warning detection system 700 for detecting undesired levels of VOCs during a drilling operation, in accordance with particular examples of the present disclosure. In the illustrated example, an undesired or maximum allowed concentration of VOCs has not been detected. It should be noted that while FIG. 7A depicts a land-based drilling system, those skilled in the art will readily recognize that the principles described herein are equally applicable to subsea drilling operations that employ floating or sea-based platforms and/or rigs, without departing from the scope of the present disclosure.

As illustrated, the system 700 may include a drilling platform 701 that supports a derrick 703 having a traveling block 705 for raising and lowering a drill string 708. A top drive or kelly 710 may support the drill string 708. A drill bit 712 may be attached to the distal end of the drill string 708 and may be driven either by a downhole motor and/or via rotation of the drill string 708 from the well surface. Without limitation, the drill bit 712 may include, roller cone bits, PDC bits, natural diamond bits, any hole openers, reamers, coring bits, and the like. As the drill bit 712 rotates, it may create the wellbore 602 that penetrates a subterranean formation 718.

The system 700 may further include a circulatory system 711 that includes a mud pump 728 to convey drilling fluid 724 from a mud pit 726 into the wellbore 602. The mud pump 728 may include pumps, compressors, or motors (e.g., surface or downhole) used to move the drilling fluid 724, as well as any valves or related joints used to regulate the pressure or flowrate of the drilling fluid 724, and any sensors (e.g., pressure, temperature, flow rate), gauges, or combinations thereof, for example.

The mud pump 728 may circulate the drilling fluid 724 through a feed pipe 730 and to a swivel 707, which may convey the drilling fluid 724 downhole through the drill string 708 and through one or more orifices in the drill bit 712. The drilling fluid 724 contacts formation fluid(s) 732 to form a downhole fluid 722. As shown, the formation fluid 732 infiltrates the wellbore 602 via the open hole section 610. The downhole fluid 722 may then be circulated back to a surface 733 via an annulus 734 defined between the drill string 708 and the wall(s) of the wellbore 602.

At the surface 733, the system 700 may also include a flow line 720 discharging the downhole fluid 722 including the drilling fluid 724 and the drill cuttings 526 onto the solids control device 501 of the system 500. The drill cuttings 526 may be gathered and subsequently analyzed with the sensor 100 of the system 500 to identify and quantify VOCs. After analysis of the drill cuttings 526 with the system 500, the drill cuttings 526 may be directed to the drill cuttings box or the receptacle 505 for disposal, as described previously with reference to FIGS. 5A-5F. The drilling fluid 724 separated via the solids control device 501 may flow into the mud pit 726 or for further downstream processing.

In certain examples, the system 700 may also include the tool 600 to analyze the downhole fluid 722 while in the wellbore 602, as previously described with reference to FIG. 6. Additionally, the cell 512 (e.g., also shown on FIG. 5A) may be placed in fluid communication with the flow line 720 to analyze the downhole fluid 722. The cell 512 may be coupled to the flow line 720, in some examples.

The system 700 may also include the system controller 524. The system controller 524 may be configured to operate the system 700. The system controller 524 may include a display 736 to display various information, such as concentrations of VOCs, for example.

Figure 7B:
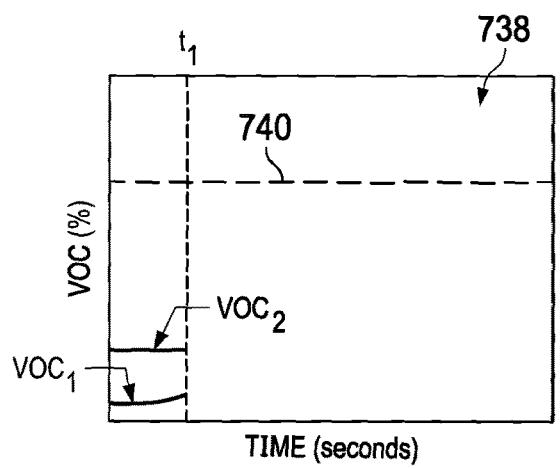
FIG. 7B illustrates a graph that shows concentrations of volatile organic compounds below a threshold, in accordance with examples of the present disclosure.

FIG. 7B illustrates a graph 738 that shows concentrations of VOCs (e.g., a first $VOC_1$, and a second $VOC_2$) detected at time $t_1$, in accordance with examples of the present disclosure. As illustrated on the graph 738, a maximum allowed VOC concentration limit 740 has not been detected.

Figure 7C:
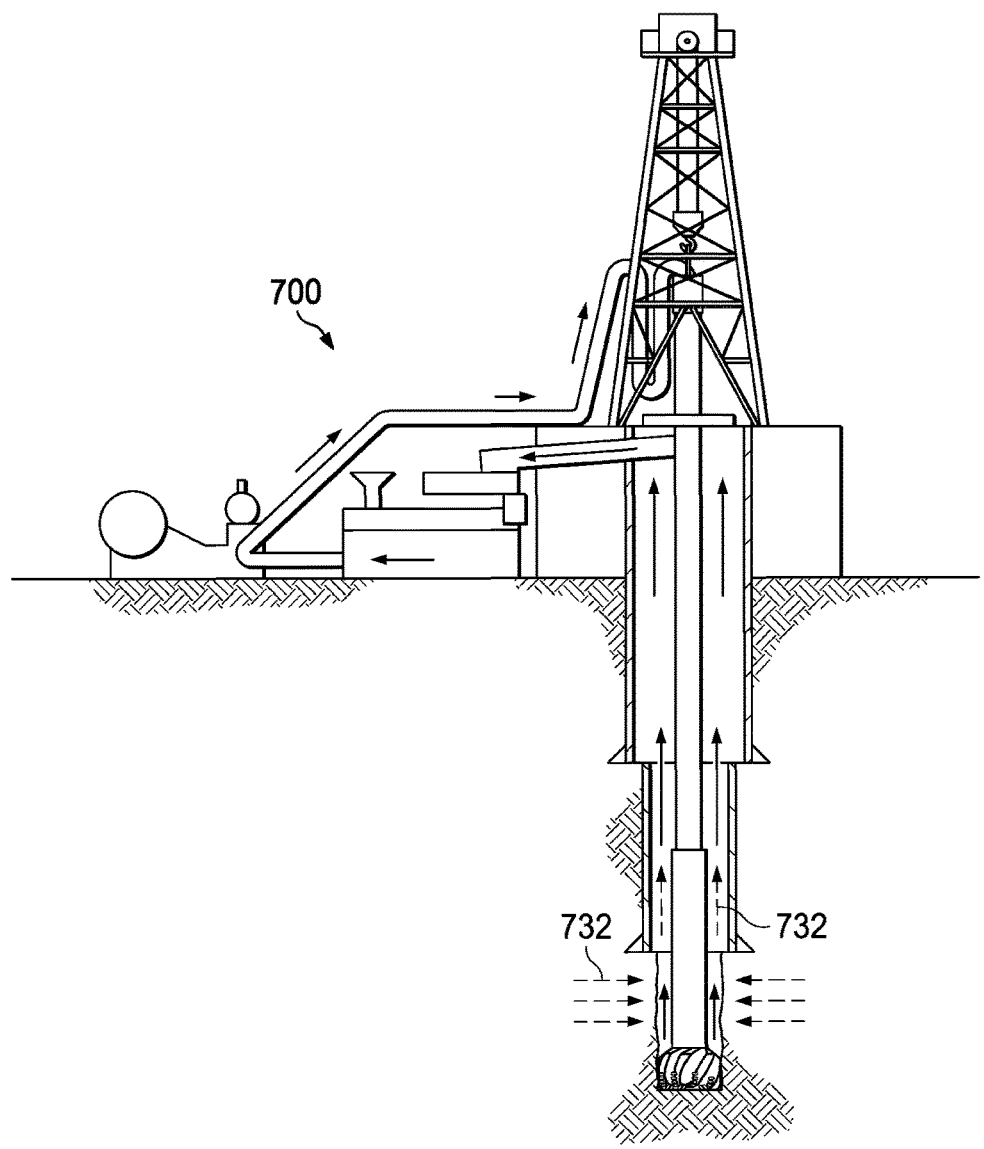
FIG. 7C illustrates the early warning detection system detecting an increase in concentrations of the volatile organic compounds, in accordance with examples of the present disclosure.

FIG. 7C illustrates the system 700 during detection of a VOC concentration that exceeds a threshold or the maximum allowed VOC concentration limit 740 (e.g., shown on FIG. 7B), in accordance with examples of the present disclosure. As time progresses, the measured quantity of detected materials may change because of an influx of the formation fluid 732. The lag time from influx until sensing with the system 700 can be modeled based on a pump rate and wellbore geometry. Thus, the measured depth of the influx of the formation fluid 732 may be approximated based on detected VOC concentrations.

Figure 7D:
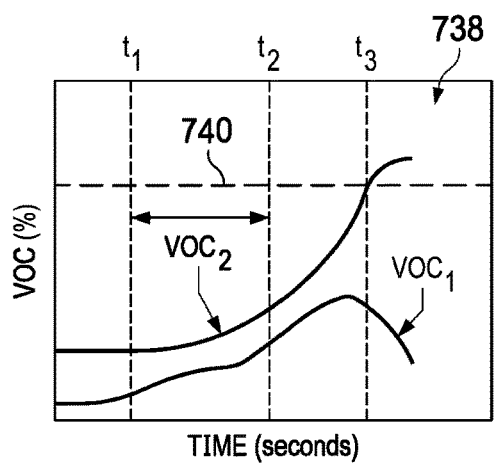
FIG. 7D illustrates a graph that shows concentrations of the volatile organic compounds exceeding the threshold, in accordance with examples of the present disclosure.

FIG. 7D illustrates the graph 738 showing detection of a VOC concentration that exceeds the limit 740, in accordance with particular examples of the present disclosure. The $VOC_1$ remains at acceptable levels. At time $t_2$, an increase of the VOC concentration is detected relative to the time $t_1$. At time $t_3$, the $VOC_2$ has increased beyond the limit 740. Rates of increase and peak measured values of VOC concentrations may be used to trigger a workflow response. In certain examples, workflow responses may include: using a choke on a flow line to increase a downhole pressure to a point that is greater than a pore pressure and/or increasing a mud density to increase a confining pressure of the mud. In some examples, the workflow response may include engaging blowout preventers.

Figure 8:
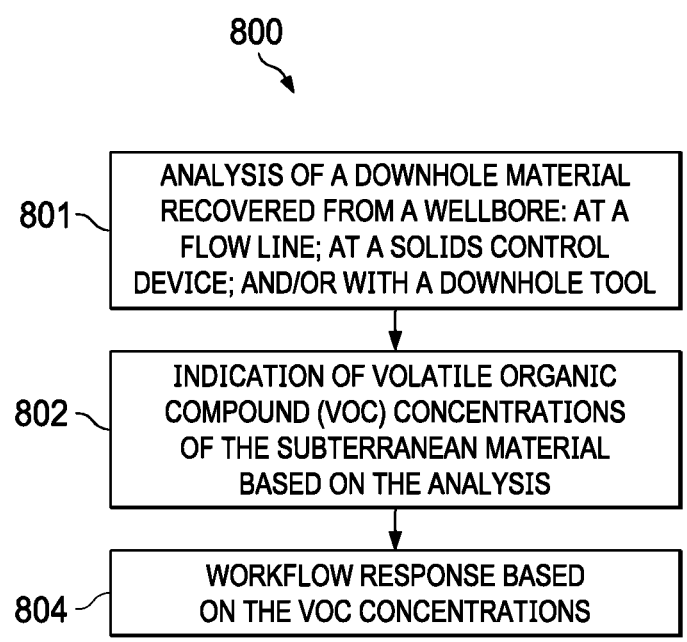
FIG. 8 illustrates an exemplary sequence for testing vapors of a downhole material recovered from a wellbore, in accordance with examples of the present disclosure.

FIG. 8 illustrates an exemplary sequence 800 for testing vapors of a downhole material recovered from a wellbore, in accordance with examples of the present disclosure.

At step 801, the downhole fluid 722 recovered from the wellbore 602 is analyzed at the flow line 720 (e.g., shown on FIGS. 7A and 7B); the drill cuttings 526 are analyzed at the solids control device 501 (e.g., shown on FIGS. 5A-5F); and/or the downhole fluid 722 is analyzed in the downhole tool 600 (e.g., shown on FIG. 6).

At step 802, the system controller 524 indicates on the display 736 VOC concentrations (e.g., shown on FIG. 7A). At step 804, the workflow responses may occur based on the VOC concentrations, as previously noted.

Accordingly, the systems and methods of the present disclosure may utilize sensors to identify and quantify material recovered from a downhole environment. The systems and methods may include any of the various features disclosed herein, including one or more of the following statements.

Statement 1. A system comprising a sensor configured to detect volatile organic compounds (VOCs), the sensor in fluid communication with a downhole material recovered from a wellbore, wherein the sensor is fluidly coupled to a circulatory system for the wellbore; and a system controller in communication with the sensor, the system controller configured to indicate concentrations of the VOCs.

Statement 2. The system of the statement 1, wherein the sensor is in fluid communication with a flow line configured to receive the downhole material from the wellbore.

Statement 3. The system of the statement 1, wherein the sensor is in fluid communication with a solids control device configured to receive the downhole material from the wellbore, the downhole material comprising downhole fluid and drill cuttings.

Statement 4. The system of the statement 3, further comprising a testing cell configured to receive the drill cuttings separated from the downhole fluid with the solids control device, wherein the sensor is fluid communication with the testing cell.

Statement 5. The system of the statement 4, wherein the testing cell includes electrical heaters configured to heat the drill cuttings to form vapors.

Statement 6. The system of the statement 4, further comprising a pretreatment tube disposed upstream to the sensor.

Statement 7. The system of the statement 6, wherein the pretreatment tube comprises a polytetrafluoroethylene tube packed with chromic acid and/or silica.

Statement 8. The system of the statement 1, further comprising a downhole tool comprising sealing pads configured to contact a wall of a wellbore, wherein the sealing pads are in fluid communication with an internal chamber of the downhole tool, wherein the sensor is disposed within the internal chamber, wherein a pressure within the internal chamber is reduceable upon instructions received from the system controller.

Statement 9. The system of the statement 8, wherein electrical heaters are disposed within the chamber.

Statement 10. A system comprising a sensor configured to detect volatile organic compounds (VOCs), the sensor in fluid communication with a downhole fluid recovered from a wellbore, wherein the sensor is fluidly coupled to at least one of a flow line, a solids control device, or a downhole tool; and a system controller in communication with the sensor, the system controller configured to indicate concentrations of the VOCs.

Statement 11. The system of the statement 10, wherein the system comprises the flow line.

Statement 12. The system of the statement 11, wherein the system comprises the solids control device comprising a testing cell, the testing cell configured to receive drill cuttings from the downhole fluid.

Statement 13. The system of the statement 12, wherein the system further comprises a first auger to direct the drill cuttings into the testing cell, the first auger configured to retract underneath a portion of the solids control device.

Statement 14. The system of the statement 13, wherein the system further comprises a second auger disposed downstream to the testing cell, the second auger configured to direct expelled drill cuttings from the testing cell into a drill cuttings box, wherein the first auger is disposed upstream to the testing cell.

Statement 15. The system of the statement 10, wherein the system comprises the downhole tool, the downhole tool comprising sealing pads in fluid communication with an internal chamber, wherein the sensor is disposed within the internal chamber, wherein the internal chamber is in fluid communication with a piston that is configured to reduce a pressure within the internal chamber.

Statement 16. A method comprising: detecting volatile organic compounds (VOCs) with a sensor that is fluidly coupled to at least one of a flow line, a solids control device, or a downhole tool; and indicating concentrations of the VOCs.

Statement 17. The method of the statement 16, further comprising detecting VOCs at the flow line.

Statement 18. The method of the statement 16, further comprising detecting VOCs with the solids control device, the solids control device comprising a testing cell configured to receive drill cuttings separated from downhole fluid with the solids control device, wherein the sensor is fluid communication with the testing cell.

Statement 19. The method of the statement 18, further comprising detecting VOCs with the downhole tool, the downhole tool comprising sealing pads configured to contact a wall of a wellbore, wherein the sealing pads are in fluid communication with an internal chamber of the downhole tool, wherein the sensor is disposed within the internal chamber.

Statement 20. The method of the statement 19, further comprising creating a vacuum in the internal chamber.

The preceding description provides various examples of the systems and methods of use disclosed herein which may contain different method steps and alternative combinations of components. It should be understood that although individual examples may be discussed herein, the present disclosure covers all combinations of the disclosed examples, including, without limitation, the different component combinations, method step combinations, and properties of the system. It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the elements that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present examples are well adapted to attain the ends and advantages mentioned as well as those that are inherent therein. The particular examples disclosed above are illustrative only and may be modified and practiced in different but equivalent manners apparent to those skilled in the art having the benefit of the teachings herein. Although individual examples are discussed, the disclosure covers all combinations of all of the examples. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of those examples. If there is any conflict in the usages of a word or term in this specification and one or more patent(s) or other documents that may be incorporated herein by reference, the definitions that are consistent with this specification should be adopted.

What is claimed is:

1. A system comprising:
   a sensor configured to detect volatile organic compounds (VOCs), the sensor in fluid communication with a downhole material recovered from a wellbore, wherein the sensor is fluidly coupled to a circulatory system for the wellbore;
   a system controller in communication with the sensor, the system controller configured to indicate concentrations of the VOCs, wherein the sensor is in fluid communication with a solids control device configured to receive a portion of the downhole material from the wellbore, the downhole material comprising downhole fluid and drill cuttings; and a testing cell configured to receive a portion of the drill cuttings separated from the downhole fluid with the solids control device, wherein the sensor is fluid communication with the testing cell.

2. The system of claim 1, further comprising a second sensor in fluid communication with a flow line, the second sensor configured to detect VOCs in the flow line.

3. The system of claim 2, wherein a portion of the downhole material is disposed in the flow line.

4. The system of claim 2, further comprising a downhole tool comprising a third sensor, the downhole tool disposed in the wellbore and configured to detect VOCs in the wellbore.

5. The system of claim 1, wherein the testing cell includes electrical heaters configured to heat the drill cuttings to form vapors.

6. The system of claim 1, further comprising a pretreatment tube disposed upstream to the sensor.

7. The system of claim 6, wherein the pretreatment tube comprises a polytetrafluoroethylene tube packed with chromic acid and/or silica.

8. The system of claim 1, further comprising a downhole tool comprising sealing pads configured to contact a wall of a wellbore, wherein the sealing pads are in fluid communication with an internal chamber of the downhole tool, wherein the sensor is disposed within the internal chamber, wherein a pressure within the internal chamber is reduceable upon instructions received from the system controller.

9. The system of claim 8, wherein electrical heaters are disposed within the chamber.

10. A system comprising:
a sensor configured to detect volatile organic compounds (VOCs), the sensor in fluid communication with a downhole fluid recovered from a wellbore, wherein the sensor is fluidly coupled to at least one of a flow line, a solids control device, or a downhole tool; and
a system controller in communication with the sensor, the system controller configured to indicate concentrations of the VOCs; and
wherein the system comprises the flow line and the solids control device, the solids control device comprising a testing cell, the testing cell configured to receive drill cuttings from the downhole fluid.

11. The system of claim 10, wherein a portion of the downhole fluid is disposed in the flow line.

12. The system of claim 11, wherein the system further comprises a first auger to direct the drill cuttings into the testing cell.

13. The system of claim 12, wherein the first auger is configured to retract underneath a portion of the solids control device.

14. The system of claim 13, wherein the system further comprises a second auger disposed downstream to the testing cell, the second auger configured to direct expelled drill cuttings from the testing cell into a drill cuttings box, wherein the first auger is disposed upstream to the testing cell.

15. The system of claim 10, wherein the system comprises the downhole tool, the downhole tool comprising sealing pads in fluid communication with an internal chamber, wherein the sensor is disposed within the internal chamber, wherein the internal chamber is in fluid communication with a piston that is configured to reduce a pressure within the internal chamber.

16. A method comprising:
detecting volatile organic compounds (VOCs) with a sensor that is fluidly coupled to at least one of a flow line, a solids control device, or a downhole tool;
indicating concentrations of the VOCs; and
detecting VOCs with the solids control device, the solids control device comprising a testing cell configured to receive drill cuttings separated from downhole fluid with the solids control device, wherein the sensor is fluid communication with the testing cell.

17. The method of claim 16, further comprising detecting VOCs at the flow line.

18. The method of claim 16, further comprising vaporizing fluid in the downhole tool.

19. The method of claim 16, further comprising detecting VOCs with the downhole tool, the downhole tool comprising sealing pads configured to contact a wall of a wellbore, wherein the sealing pads are in fluid communication with an internal chamber of the downhole tool, wherein the sensor is disposed within the internal chamber.

20. The method of claim 19, further comprising creating a vacuum in the internal chamber.

* * * * *